US00PP16873P2

(12) United States Plant Patent
Pieters

(10) Patent No.: US PP16,873 P2
(45) Date of Patent: Jul. 25, 2006

(54) ***CHRYSANTHEMUM* PLANT NAMED 'GEDI THREE PS'**

(50) Latin Name: *Chrysanthemum morifolium*
Varietal Denomination: Gedi Three PS

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 11/117,947

(22) Filed: Apr. 28, 2005

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

PP13,455 P2 * 1/2003 Pieters
PP13,797 P2 * 5/2003 Pieters

* cited by examiner

*Primary Examiner*—Kent L. Bell
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by flowers with golden yellow ray florets that have a darker golden center before the flower fully opens. The plant is freely branching, highly flexible, and has a mounding growth habit.

1 Drawing Sheet

Figure 1:
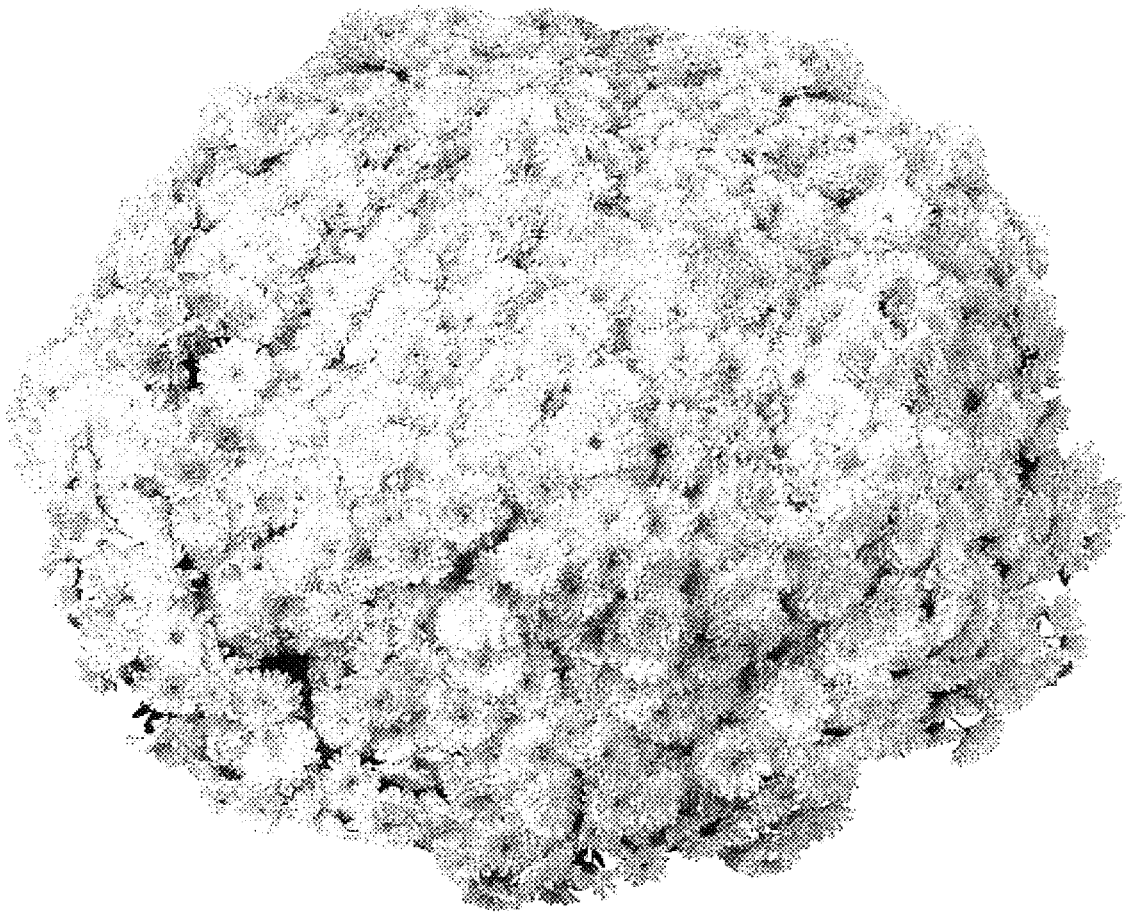

Latin name of the genus and species: *Chrysanthemum morifolium.*
Variety denomination: 'Gedi Three PS'.

BACKGROUND OF THE INVENTION

The new cultivar is a product of hybridization of a female parent *Chrysanthemum* plant variety '95 252 05' (unpatented, undistributed seedling) and a male parent *Chrysanthemum* plant variety '95 076 02' (unpatented, undistributed seedling). The new cultivar was discovered and selected by Dirk Pieters in September, 1999 In Oostniewkerke, Belgium.

Asexual reproduction of the new cultivar 'Gedi Three PS' by terminal cuttings and tissue culture was performed in Oxnard, Ventura County, Calif., and has shown that the unique features of this cultivar are stable and reproduced true to type on successive generations.

SUMMARY OF THE INVENTION

The cultivar 'Gedi Three PS' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Three PS.' These characteristics in combination distinguish 'Gedi Three PS' as a new and distinct *Chrysanthemum* cultivar:

1. The flowers have golden yellow ray florets and a darker golden center before fully opening.
2. The plant has a mounding growth habit.
3. The plant is free branching.
4. The plant has a highly flexible plant habit.

Plants of the new cultivar 'Gedi Three PS' are similar to plants of the female parent variety '95 252 05' in most horticultural characteristics, however plants of the new cultivar 'Gedi Three PS' have a larger diameter flower and darker yellow florets. Plants of the new cultivar are also shorter and have an earlier natural season blooming response than plants of the female parent variety.

Plants of the new cultivar 'Gedi Three PS' are similar to plants of the male parent variety, '95 076 02,' in most horticultural characteristics. However, plants of the new cultivar 'Gedi Three PS' have a smaller diameter flower and darker yellow ray florets than plants of the male parent variety. In addition, plants of the new variety 'Gedi Three PS' are shorter and have an earlier natural season blooming response than plants of the male parent variety.

In comparison to the commercially available variety 'Gedi One Ces' (U.S. Plant Pat. No. 13,797) the flowers of the new variety 'Gedi Three PS' have fewer ray florets that are darker yellow in color than the comparable variety. Additionally, the new variety 'Gedi Three PS' blooms earlier than the comparable variety. Further, the leaf of the new variety 'Gedi Three PS' is wider and shorter than the leaf of the comparable variety 'Gedi One Ces.'

In comparison to the commercially available variety 'Gedi One Avi' (U.S. Plant Pat. No. 13,455) the new variety 'Gedi Three PS' has darker yellow ray florets, and has about 13 more flowers per stem than the comparable variety. Additionally, the flower of the new variety has less ray florets than the comparable variety 'Gedi One Avi.' Further, the flower of the new variety 'Gedi Three PS' lasts approximately five to seven day longer than the comparable variety 'Gedi One Avi.'

BRIEF DESCRIPTION OF THE PHOTOGRAPH

The accompanying photograph in FIG. 1 illustrates in full color a typical plant of 'Gedi Three PS' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three PS' plants grown in a greenhouse in Oxnard, Calif. during the month of September 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three PS.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 28.5 cm.
Plant spread: Approximately 34 cm.
Growth rate: Moderate.
Branching characteristics: Free branching.
Length of lateral branches: Approximately 24 cm.
Number of leaves per lateral branch: Approximately 17.
Age of plant described: Approximately 135 days from a rooted cutting.

FOLIAGE

Leaf:
- *Arrangement.*—Alternate.
- *Average length.*—Approximately 5.7 cm.
- *Average width.*—Approximately 4.9 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 2.8 cm.
- *Color.*—Young foliage upper side: Near Green 138A. Young foliage under side: Near Green 138B. Mature foliage upper side: Near Green 137B. Mature foliage under side: Near Green 137B.
- *Leaf venation.*—Type: Palmately net. Venation color upper side: Near Green 138B. Venation color under side: Near Green 138B.

Petiole:
- *Average length.*—Approximately 2.1 cm.
- *Color.*—Near Green 137B.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Form.*—Decorative.
- *Natural flowering season.*—Approximately the last week of August through the first week of September.
- *Number of flowers per lateral branch.*—Approximately 25.
- *Diameter.*—Approximately 5.5 cm.
- *Depth.*—Approximately 2.7 cm.
- *Longevity on plant.*—Approximately 27 days.
- *Persistence.*—Persistent.

Ray florets:
- *Appearance.*—Matte.
- *Texture.*—Smooth.
- *Average number of ray florets per flower.*—Approximately 175.
- *Shape.*—Oblong.
- *Aspect.*—Flat.
- *Margin.*—Entire.
- *Apex.*—Retuse.
- *Length.*—Approximately 2.9 cm.
- *Width.*—Approximately 0.9 cm.
- *Color.*—Upper surface at first opening: Near Yellow 12A. Upper surface at maturity: Near Yellow 11A. Upper surface at fading: Near Yellow 10B. Under surface at first opening: Near Yellow 12B. Under surface at maturity: Near Yellow 10A. Under surface at fading: Near Yellow 11B.

Disc forets:
- *Appearance.*—Shiny.
- *Texture.*—Smooth.
- *Average number of disc florets per disc.*—Approximately 20.
- *Shape.*—Cylindric.
- *Apex.*—Obtuse.
- *Average length.*—Approximately 0.8 cm.
- *Average width.*—Approximately 0.1 cm.
- *Color.*—At first opening: Near Yellow 7A. At maturity: Near Yellow 4C. At fading: Near Yellow-orange 14D.

Peduncle:
- *Length.*—At terminal end (shortest): Approximately 3.1 cm. At lateral end (longest): Approximately 6.1 cm.
- *Angle to stem.*—Acute.
- *Strength.*—Moderate.
- *Color.*—Near Green 138A.
- *Habit.*—Upright.
- *Diameter.*—Approximately 0.2 cm.
- *Surface texture.*—Lightly pubescent.

Flower bud:
- *Length.*—Approximately 0.9 cm.
- *Diameter.*—Approximately 0.8 cm.
- *Form.*—Globular.
- *Color.*—Near Orange 26A.

Involucral bracts (phyllaries):
- *Appearance.*—Matte.
- *Texture.*—Lightly pubescent.
- *Number.*—Approximately 20.
- *Shape.*—Oblanceolate.
- *Margin.*—Entire.
- *Apex.*—Acute.
- *Length.*—Approximately 0.8 cm.

*Width.*—Approximately 0.8 cm.
*Color.*—Upper side: Near Green 138A. Under side: Near Green 138A.

REPRODUCTIVE ORGANS

Ray florets:
*Number of pistils per floret.*—1.
*Stigma shape.*—2 branched.
*Stigma color.*—Near Yellow 7A.
*Style color.*—Near Yellow 2A.
*Style length.*—Approximately 0.9 cm.
*Stamens.*—Absent.

Disc florets:
*Number of pistils per floret.*—1.
*Stigma shape.*—Two-branched.
*Stigma color.*—Near Yellow 4C.
*Style length.*—Approximately 0.3 cm.
*Style color.*—Near Yellow-green 154D.
*Number of stamens per floret.*—Approximately 5.
*Anther shape.*—Tubular.
*Anther color.*—Near Yellow 5B.
*Pollen color.*—Near Yellow 7A.

OTHER CHARACTERISTICS

Disease resistance: Neither resistance nor susceptibility has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of about 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three PS' as herein illustrated and described.

* * * * *